United States Patent
Bragulla (12)

(10) Patent No.: US 6,351,866 B1
(45) Date of Patent: Mar. 5, 2002

(54) ARM SCRUBBING SYSTEM

(76) Inventor: Reiner George Bragulla, 1480 Gulf Blvd. - #206, Clearwater, FL (US) 33767

( * ) Notice: Subject to any disclaimer, the term of this patent is extended or adjusted under 35 U.S.C. 154(b) by 0 days.

(21) Appl. No.: 09/945,080

(22) Filed: Aug. 31, 2001

(51) Int. Cl.[7] .......................... A47L 25/00; A47K 7/04; A46B 13/04
(52) U.S. Cl. .......................... 15/21.1; 15/88.4; 134/180
(58) Field of Search ................................ 15/21.1, 88.4; 134/95.2, 180, 181

(56) References Cited

U.S. PATENT DOCUMENTS

| | | | |
|---|---|---|---|
| 4,564,968 A | * | 1/1986 | Buckley |
| 5,611,099 A | * | 3/1997 | Kelly |
| 5,894,619 A | * | 4/1999 | Hougland |
| 5,924,148 A | * | 7/1999 | Flowers, Jr. |

* cited by examiner

Primary Examiner—Randall E. Chin

(57) ABSTRACT

An arm scrubbing system comprises a housing. The housing has upper, lower, distal, proximal and side walls. The walls define a chamber. Two circular rear apertures are formed in the distal wall and two circular proximal apertures are formed in the proximal wall. A pair of plastic transparent tubes are provided. Each tube has a distal end and a proximal end. A plurality of tufts secured to the interior face of each tube define openings. Further provided is a plurality of apertures through the tubes between the tufts for the passage of cleansing/disinfectant fluid a from the chamber into the tubes for cleaning the arms of a user. Provided last is a drive assembly. The drive assembly includes a motor with drive pulleys. The drive assembly further includes driven pulleys extending distally from each tube. A drive belt couples the drive pulleys and the driven pulleys.

5 Claims, 3 Drawing Sheets

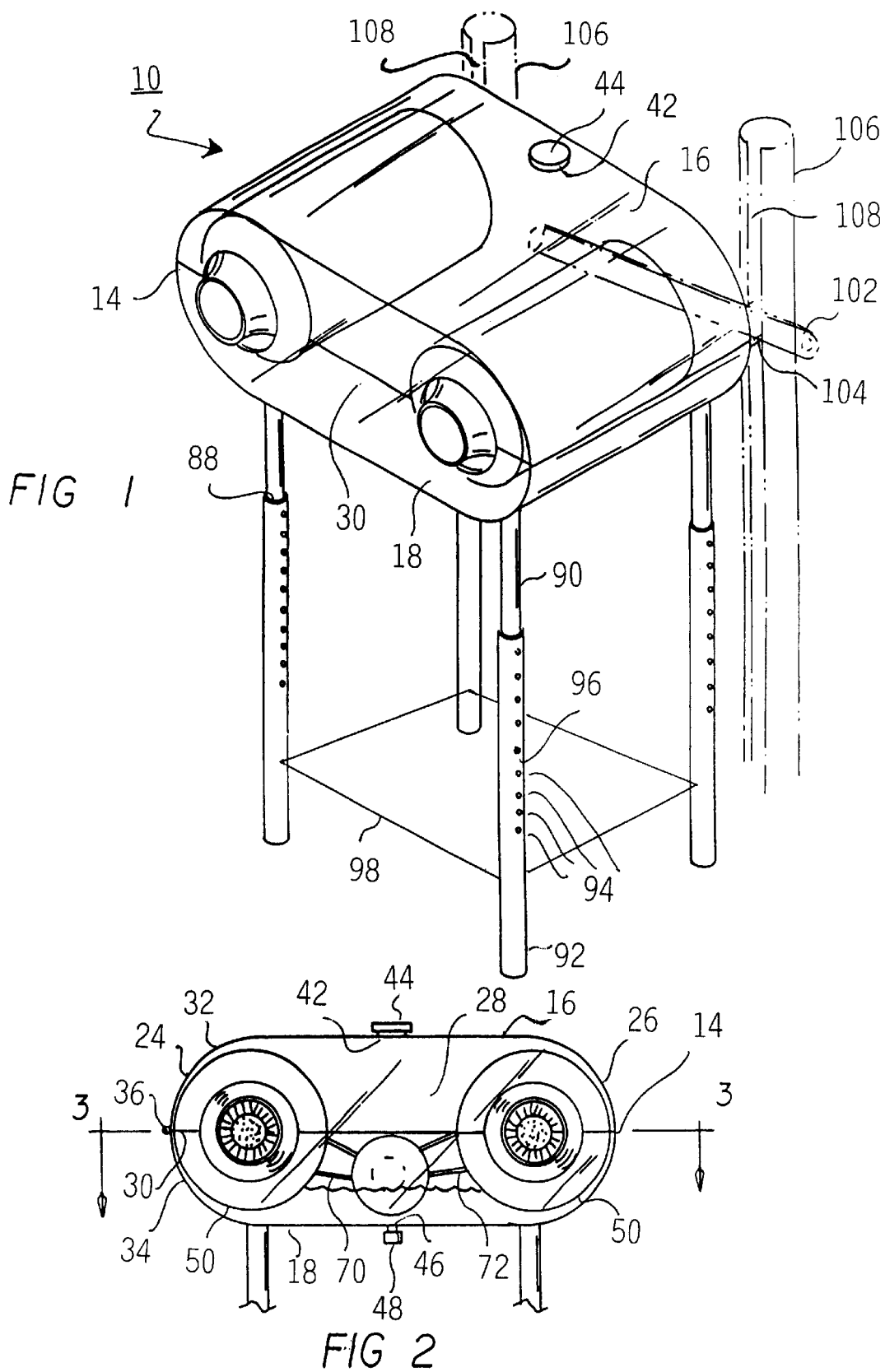

ARM SCRUBBING SYSTEM

BACKGROUND OF THE INVENTION

1. Field of the Invention

The present invention relates to a arm scrubbing system and more particularly pertains to automatically cleaning the arms, hands and fingernails of a surgeon prior to contact with a patient.

2. Description of the Prior Art

The use of cleaning systems of known designs and configurations is known in the prior art. More specifically, cleaning systems of known designs and configurations previously devised and utilized for the purpose of scrubbing a surgeon's hands and/or, fingers and/or fingernails through known methods and apparatuses are known to consist basically of familiar, expected, and obvious structural configurations, notwithstanding the myriad of designs encompassed by the crowded prior art which has been developed for the fulfillment of countless objectives and requirements.

By way of example, U.S. Pat. No. 3,918,117 to Plante discloses a surgical washing device. U.S. Pat. No. 3,918,987 to Kopfer discloses a surgeon hand arm scrubbing apparatus. U.S. Pat. No. 4,564,968 to Buckley discloses a hand-cleaning device. U.S. Pat. No. 4,817,651 to Crisp et al discloses hand and forearm cleansing apparatus. Lastly, U.S. Pat. No. 6,141,811 to Nakamura discloses an automatic hand washer.

While these devices fulfill their respective, particular objectives and requirements, the aforementioned patents do not describe a arm scrubbing system that allows automatically cleaning the arms, hands and fingernails of a surgeon prior to contact with a patient.

In this respect, the arm scrubbing system according to the present invention substantially departs from the conventional concepts and designs of the prior art, and in doing so provides an apparatus primarily developed for the purpose of automatically cleaning the arms, hands and fingernails of a surgeon prior to contact with a patient.

Therefore, it can be appreciated that there exists a continuing need for a new and improved arm scrubbing system which can be used for automatically cleaning the arms, hands and fingernails of a surgeon prior to contact with a patient. In this regard, the present invention substantially fulfills this need.

SUMMARY OF THE INVENTION

In view of the foregoing disadvantages inherent in the known types of cleaning systems of known designs and configurations now present in the prior art, the present invention provides an improved arm scrubbing system. As such, the general purpose of the present invention, which will be described subsequently in greater detail, is to provide a new and improved arm scrubbing system and method which has all the advantages of the prior art and none of the disadvantages.

To attain this, the present invention essentially comprises a housing. The housing is fabricated of a transparent plastic material. The housing has a planar upper wall and a parallel planar lower wall and a planar distal wall and a parallel planar proximal wall. Semi-cylindrical side walls are provided there between. The housing has a chamber between the walls. The housing also has a horizontal parting line. The horizontal parting line separates the housing into an upper half and a similarly configured lower half. A hinge couples the upper and lower halves along the horizontal parting line of one side wall. In this manner access is allowed to the chamber. Two laterally spaced circular rear apertures are formed in the distal wall and two laterally spaced circular front apertures are formed in the proximal wall. Each aperture has an upper semi-circle in the upper half and a lower semi-circle in the lower half. Provided next is a circular opening. The circular opening is formed in the upper wall for adding cleansing/disinfectant fluid into the chamber. A stopper is positionable in the circular opening. A second circular opening is formed in the lower wall for removing cleansing/disinfectant fluid from the chamber. Another stopper is positionable in the second circular opening. A pair of similarly configured plastic transparent tubes is provided. The tubes are in a cylindrical configuration. Each tube has a distal end. The distal end is rotatably received in a distal aperture. A proximal end is rotatably received in a proximal aperture for concurrent oscillary movement of the tubes within the chamber. Next provided is a plurality of tufts of bristles. The bristles are radially exterior ends are secured to the interior face of each tube. Radially interior ends are defined openings for the receipt of the arms of a surgeon. A plurality of apertures is provided through the tubes between the tufts for the passage of cleansing/disinfectant fluid from the chamber into the tubes for cleaning the arms of a surgeon. A drive assembly is provided next. The drive assembly includes a motor operable in an oscillatory manner. The motor is secured to the distal wall with drive pulleys extending distally therefrom. A driven pulley extends distally from each tube. A drive belt couples the drive pulleys and the distal pulleys. An elastomeric washer-like member is further provided. The washer-like member is in a generally frusto-concial configuration fixedly secured to the proximal wall coaxial with the tubes for the passage of a surgeon arms there through. Provided next is a vertically disposed finger washing plate. The finger washing plate is axially slidable within each tube adjacent to the distal wall. Each plate has four radially extending fingers with enlarged exterior ends. Each plate also has keyways formed with respect to each cylinder for receiving the exterior ends of the fingers. Coil springs are provided within the keyways urging the exterior ends and plate proximally. The plate has proximally extending bristles for washing the fingers and fingernails of a surgeon. Further provided are four downwardly extending legs. The legs depend from the four corners of the lower wall. Each leg has an upper segment and a tubular lower segment. Each leg further has spaced holes and is slidably received over an associated upper segment. A spring biased button extends from the upper leg through a preselected hole in the lower leg. A stabilizing plate couples the lower legs adjacent to their lower ends. Last provided is a horizontal adjustment rod. The rod is secured to the distal wall with distally extending projections and a pair of hollow guide rails with vertical slots receiving the projections for varying the height of the housing.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved arm scrubbing system which has all of the advantages of the prior art cleaning systems of known designs and configurations and none of the disadvantages.

It is another object of the present invention to provide a new and improved arm scrubbing system which may be easily and efficiently manufactured and marketed.

It is further an object of the present invention to provide a new and improved arm scrubbing system which is of durable and reliable constructions.

An even further object of the present invention is to provide a new and improved arm scrubbing system which is susceptible of a low cost of manufacture with regard to both materials and labor, and which accordingly is then susceptible of low prices of sale to the consuming public, thereby making such arm scrubbing system economically available to the buying public.

Even still another object of the present invention is to provide a arm scrubbing system for automatically cleaning the arms, hands and fingernails of a surgeon prior to contact with a patient.

Lastly, it is an object of the present invention to provide a new and improved arm scrubbing system comprising a housing. The housing has upper, lower, distal, proximal and side walls. The walls define a chamber. Two circular rear apertures are formed in the distal wall and two circular proximal apertures are formed in the proximal wall. A pair of plastic transparent tubes are provided. Each tube has a distal end and a proximal end. A plurality of tufts secured to the interior face of each tube define openings. Further provided is a plurality of apertures through the tubes between the tufts for the passage of cleansing/disinfectant fluid from the chamber into the tubes for cleaning the arms of a user. Provided last is a drive assembly. The drive assembly includes a motor with drive pulleys. The drive assembly further includes driven pulleys extending distally from each tube. A drive belt couples the drive pulleys and the driven pulleys.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a perspective illustration of the arm scrubbing system constructed in accordance with the present invention.

FIG. 2 is a from elevational view of the system shown in FIG. 1.

The same reference numerals refer to the same parts throughout the various Figures.

DESCRIPTION OF THE PREFERRED EMBODIMENT

Figure 3:
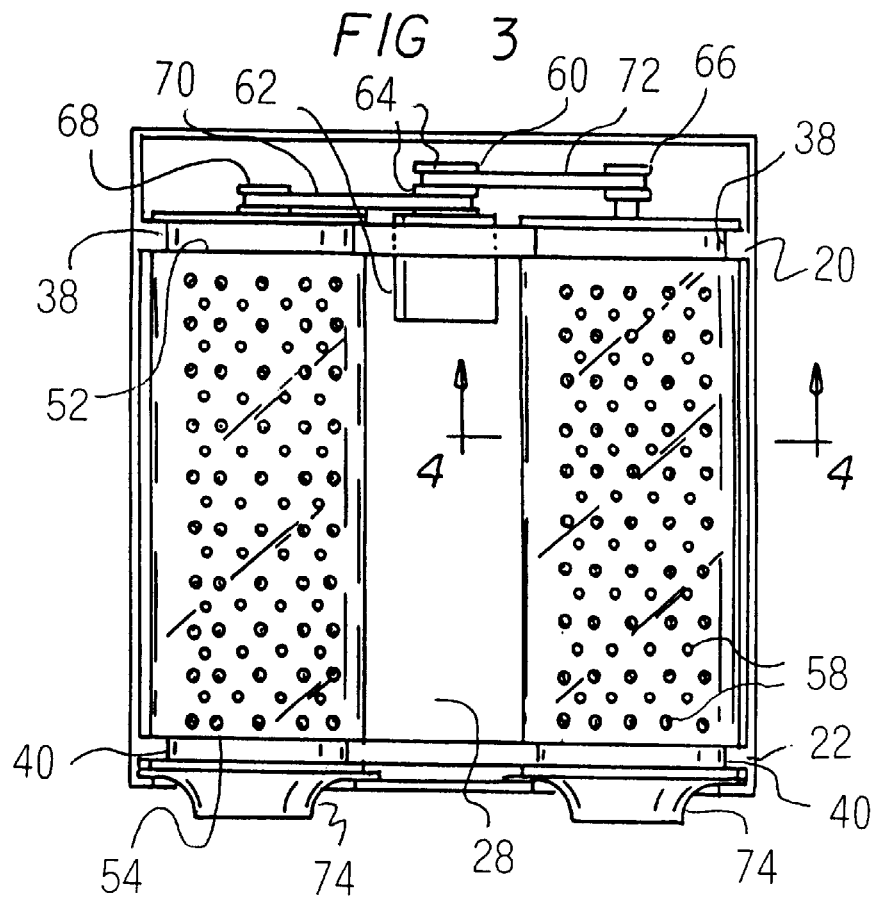
FIG. 3 is a cross-sectional view taken along line 3—3 of FIG. 2.
Figure 4:
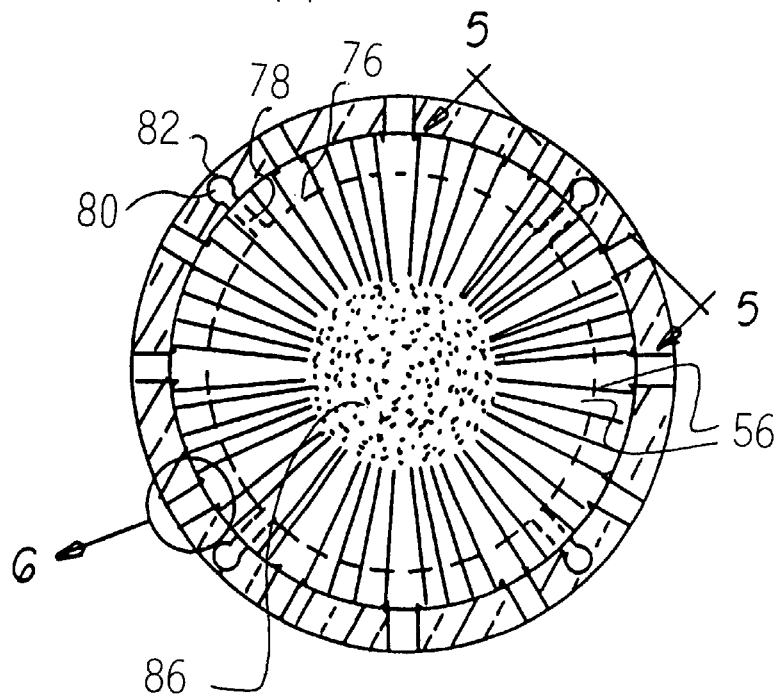
FIG. 4 is a cross-sectional view taken along line 4—4 of FIG. 3.
Figure 5:
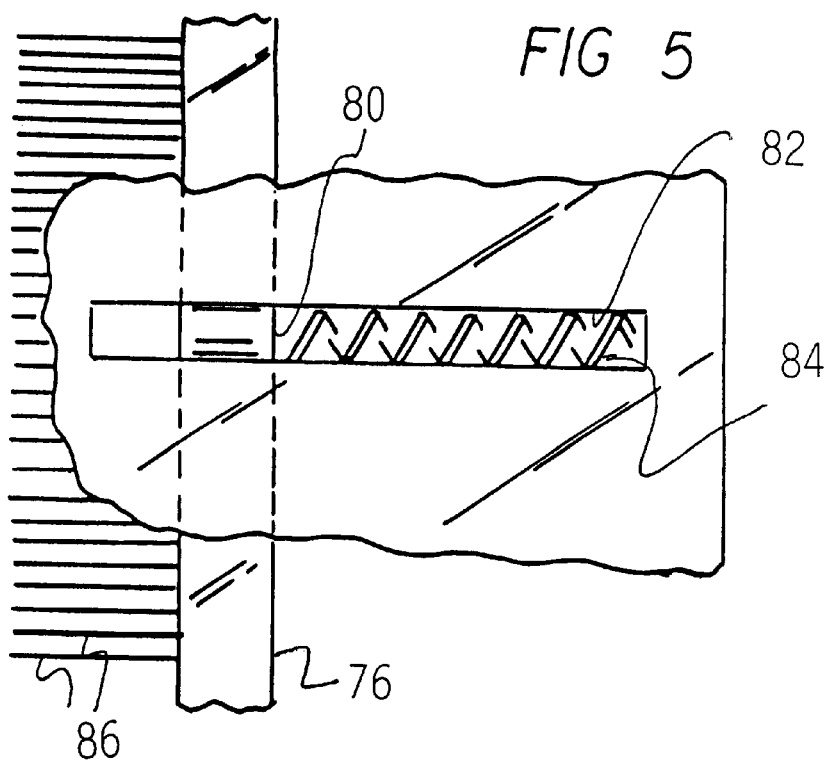
FIG. 5 is a cross-sectional view taken along line 5—5 of FIG. 4.
Figure 6:
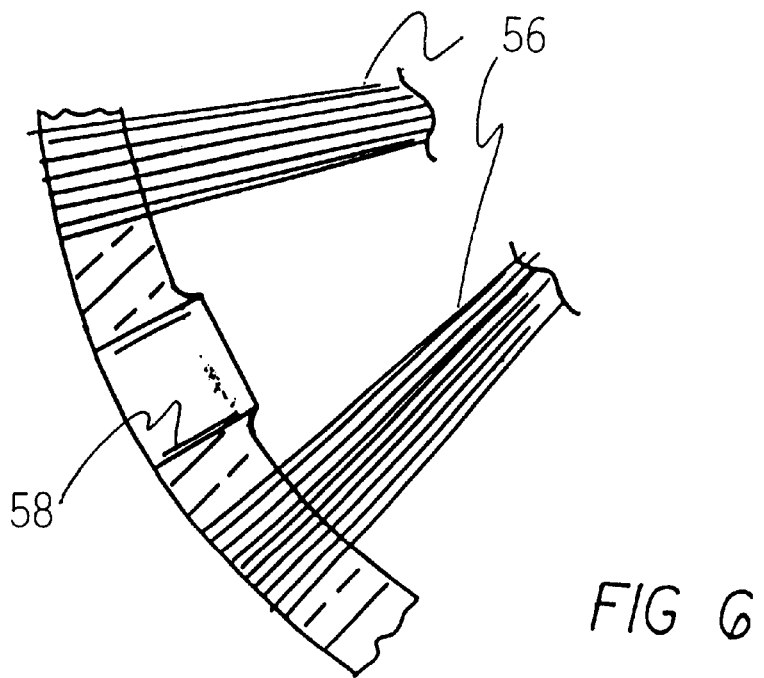
FIG. 6 is an enlarged view of a hole and tufts taken at circle 6 of FIG. 4.

With reference now to the drawings, and in particular to FIG. 1 thereof, the preferred embodiment of the new and improved arm scrubbing system embodying the principles and concepts of the present invention and generally designated by the reference numeral 10 will be described.

The present invention, the arm scrubbing system 10 is comprised of a plurality of components. Such components in their broadest context include a housing, a pair of plastic transparent tubes, a plurality of tufts, a plurality of apertures and a drive assembly. Such components are individually configured and correlated with respect to each other so as to attain the desired objective.

First provided is a housing 14. The housing is fabricated of a transparent plastic material. The housing has a planar upper wall 16 and a parallel planar lower wall 18 and a planar distal wall 20 and a parallel planar proximal wall 22. Semi-cylindrical side walls 24, 26 are provided there between. The housing has a chamber 28 between the walls. The housing also has a horizontal parting line 30. The horizontal parting line separates the housing into an upper half 32 and a similarly configured lower half 34. A hinge 36 couples the upper and lower halves along the horizontal parting line of one side wall. In this manner access is allowed to the chamber. Two laterally spaced circular rear apertures 38 are formed in the distal wall and two laterally spaced circular front apertures 40 are formed in the proximal wall. Each aperture has an upper semi-circle in the upper half and a lower semi-circle in the lower half.

Provided next is a circular opening 42. The circular opening is formed in the upper wall for adding cleansing/disinfectant fluid into the chamber. A stopper 44 is positionable in the circular opening. A second circular opening 46 is formed in the lower wall for removing cleansing/disinfectant fluid from the chamber. Anotherstopper stopper 48 is positionable in the second circular opening. These openings may be coupled to pumps for the automatic dispensing and removal of various fluids as may be needed.

A pair of similarly configured plastic transparent tubes 50 is provided. The tubes are in a cylindrical configuration. Each tube has a distal end 52. The distal end is rotatably received in a distal aperture. A proximal end 54 is rotatably received in a proximal aperture for concurrent oscillary movement of the tubes within the chamber.

Next provided is a plurality of tufts 56 of bristles. The bristles radially exterior ends are secured to the interior face of each tube. Radially interior ends are defined openings for the receipt of the arms of a surgeon. The bristles may be formed with their radially exterior ends within the tubes. In the alternative, each tuft or grouping of bristles may be on a cylindrical plug removable from the tube so that one or more plugs may be removed to replace any group of bristles as may be needed. Further, the radially interior ends of the tufts may be frusto-conical to accommodate arms which are larger at the proximal end and smaller at the distal end.

A plurality of apertures 58 is provided through the tubes between the tufts for the passage of cleansing/disinfectant fluid from the chamber into the tubes for cleaning the arms of a surgeon.

A drive assembly 60 is provided next. The drive assembly includes a motor 62 operable in an oscillatory manner. The motor is secured to the distal wall with drive pulleys 64 extending distally therefrom. A driven pulley 66, 68 extends distally from each tube. A drive belt 70, 72 couples the drive pulleys and the distal pulleys.

An elastomeric washer-like member 74 is further provided. The washer-like member is in a generally frusto-concial configuration fixedly secured to the proximal wall coaxial with the tubes for the passage of a surgeon arms there through.

Provided next is a vertically disposed finger washing plate 76. The finger washing plate is axially slidable within each tube-adjacent to the distal wall. Each plate has four radially extending fingers 78 with enlarged exterior ends 80. Each plate also has keyways 82 formed with respect to each cylinder for receiving the exterior ends of the fingers. Coil springs 84 are provided within the keyways urging the exterior ends and plate proximally. The plate has proximally extending bristles 86 for washing the fingers and fingernails of a surgeon. The keyways may be formed in the tubes for convenience or as separate elements within the tubes for greater rigidity.

Further provided are four downwardly extending legs 88. The legs depend from the four corners of the lower wall. Each leg has an upper segment 90 and a tubular lower segment 92. Each leg further has spaced holes 94 and is slidably received over an associated upper segment. A spring biased button 96 extends from the upper leg through a preselected hole in the lower leg. A stabilizing plate 98 couples the lower legs adjacent to their lower ends.

Last provided, as an alternate or supplemental height changer, is a horizontal adjustment rod 102. The rod is secured to the distal wall with distally extending projections 104 and a pair of hollow guide rails 106 with vertical slots 108 receiving the projections for varying the height of the housing.

From the foregoing, it can be understood that the present invention relates to automatic brush-washing machines, specifically for the purpose of hygienically cleaning, brushing and disinfecting hands and arms of persons engaged in various fields including hospital-operating theaters, in the processing of raw foods or handling of other materials, that are sensitive and can become contaminated by touch of unclean human hands or arms.

By way of example, before a surgeon in a hospital may conduct a surgical procedure in an operating theater, he has to scrub his hands, fingers, fingernails and his arms up to the elbow for a period of a minimum of 10–15 minutes with a disinfecting soap or soap-type solution. This scrubbing and cleaning process is conducted with running warm water and a manual hand brush is used for this purpose. After the manual brushing process is completed, the surgeon rinses his hands and arms under clean warm water and thereafter usually rinses with or, applies a disinfecting solution or cream to his hands and arms.

The above described process is very time-consuming and costly, considering a doctor's salary, and especially in cases of emergency, it is a sometimes life-depending lengthy process. The manual hand brush has only a small surface area, which is applied to arms and hands from spot to spot with stroking movements and his thoroughness, which determine the results of his cleaning his hands and arms.

Also in the food-processing and handling business, it is important for employees to always have properly cleansed hands, free of contaminating bacteria or other contaminants. Salmonella, e-coli bacteria or just plain dirt and loose skin can contaminate fresh produce of any kind. The casual hand wash, presently conducted by employees, is insufficient to ensure proper food-handling procedure and hygiene.

The present invention relates to an automatic electrically driven mechanical brushing and scrubbing machine, which-cleanses and brushes arms, and/or hands, fingers and fingernails. The machine is a waterproof box-like construction with two closed-ended tubes inserted inside the box. The box has a hinged opening to the top side for cleaning and replacement of the brush-tubes. The box has two round openings to the front, to which the tube-openings are attached. The tubes are fitted with brushes formed of tufts all around the inside and at the closing end of the tubes. The brushes are long and bendable. Opposing each other in the tube, they are leaving an opening in the middle of the box of at least 1 to 2 inches. The tubes are open on one side so that hands and arms can be inserted. These openings are fitted to the box-openings. The tubes are closed on the end-side. The closed end-sides of the tubes are adjustable to a person's arms-length.

The box and the tubes are preferably made out of a clear type plastic material and the brushes are made out of a clear type nylon or other clear material. This is an important aspect, as the person inserting his hands and arms into the tubes will want to be able to watch the washing process.

The entrance openings of the tubes have a flexible plastic-rubber type shield with an expandable opening, through which the hands and/or arms are inserted. The plastic-rubber shield is to prevent outside spillage of washing solution. The tubes have holes all along their sides for water, wash solution and disinfecting solutions to enter the tubes during the washing, brushing and rinsing cycle. The tubes are attached inside the box with ball bearings or similar turning parts and are being turned and driven by an electric motor in a circular motion, simulating the previous manual brushing operation. In a machine for hand-only cleaning, the tubes are shorter in length than the tubes for a machine required for a total hands plus arm-to-elbow cleaning.

By using a continuous rotary brushing movement, or a rotary brushing, which is changing from right turn to left turn and reverse like a windscreen wiper motor after very part-turn or couple of turns, a thorough brushing and cleansing of hands and arms is assured. The end-closings of the tubes are pre-adjustable to the length of the person's arm and hands and is fitted with harder, shorter and more solid type of bristle, so that hands and especially fingernails can be properly cleansed. The machine is free-standing or attached to guide rails onto a wall. It is connected to hot and cold water supply and electricity with flexible piping. The machine can be adjusted for the height of the person using it. All valves, motors and pumps employed in the working of the machine will be of low-voltage, or otherwise properly isolated, so as not to endanger anybody using the machine.

The machine is attached with pipes or tubing to containers for feeding it with a liquid soap-wash solution and disinfecting solutions. The solutions shall be fed into the machine by gravity flow, a feeder-pump or a valve at settable proportions relative to the amount of after being used.

When a doctor, food handler, or other person wants to cleanse and disinfect their hands and/or arms, they insert their hands and arms into the two brush-tubes of the machine. A motion sensor or switch will detect this and activate a water-inlet valve or pump. At the same time a wash-soap solution is being inserted into the box. When the water-soap solution has filled the wash-box to a certain level, the machines brushing tubes are activated and continue with their brushing cycle for a certain amount of time, settable for between 10 seconds to 300 seconds in duration. The speed of the motor driven brush-tubes in predetermined and settable and variable. The washing solution, which is partly or completely covering the holes in the tubes, is now being leaked into the tubes through those holes. The wash-solution is wetting and penetrating the brushes and bristles inside the tube and through the rotary movement of the tubes, the hands and arms are now thoroughly brushed and cleansed. By pressing the extended fingers against the brushes at the back-end of the tubes, the fingernails are properly cleansed, the same applies for the flat and extended hands.

After the washing cycle has been completed, the now dirty water may be drained out of the machine manually or by means of an exit-valve and/or pump. As soon as the water is drained, the first rinsing process will be started. Fresh clean water may fill the box to a certain level and machines brush-tubes will be activated again, cleansing away any remaining soap and wash solution of the previous washing cycle. After about 10 to 60 seconds of this first rinsing process, the rinse water will be drained off and the second rinsing cycle will be activated. During the second rinsing cycle, a disinfecting solution (e.g. $H_2O_2$, is inserted together with the fresh water in certain proportions. The brush-tubes will be activated as usual. The second rinsing solution thus contains anti-bacterial and disinfecting properties. The duration of the second rinsing cycle can be settable of between 10 second to 300 seconds.

When the second rinsing process has been completed, the brush-tubes will stop and the last solution will be drained from the machine. The person can now remove his arms from the tubes and is properly cleansed and disinfected.

As the brush-tubes provide a far larger surface area, up to 50 times more, than a presently used hand brush and as the rotary circular motion of the motor driven brush-tubes is much faster, up to 100 times faster, than can be done manually, the whole washing, rinsing and disinfections process as done by the invention is superior in speed and thoroughness.

The whole process can be achieved in between 1 to 4 minutes, thus saving the hospital time and lots of money. In cases of emergency, a doctor's hands can now be scrubbed, disinfected and ready for operation within a very short period of time, time that is costly and can be vital and life saving.

The same applies to food-handlers or other people, working with contaminant sensitive material. Hands need to be cleaned properly and thoroughly. It is faster and easier for an employee to stick their hands into an automatic washing machine, than to just casually wash them under running water. Now companies can make it mandatory for employees to wash and disinfect their hands before handling foods or other sensitive materials.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. An arm scrubbing system for automatically cleaning the arms, hands and fingernails of a surgeon prior to contact with a patient comprising, in combination:

a housing fabricated of a transparent plastic material with a planar upper wall and a parallel planar lower wall and a planar distal wall and a parallel planar proximal wall and with semi-cylindrical side walls there between, the housing having a chamber between the walls and a horizontal parting line separating the housing into an upper half and a similarly configured lower half, a hinge coupling the upper and lower halves along the horizontal parting line of one side wall to allow access to the chamber, two laterally spaced circular rear apertures formed in the distal wall and two laterally spaced circular front apertures formed in the proximal wall, each aperture having an upper semi-circle in the upper half and a lower semi-circle in the lower half;

a circular opening formed in the upper wall for adding cleansing/disinfectant fluid into the chamber with a stopper positionable there within and a second circular opening formed in the lower wall for removing cleansing/disinfectant fluid from the chamber with a stopper positionable there within;

a pair of similarly configured plastic transparent tubes in a cylindrical configuration, each tube having a distal end rotatably received in a distal aperture and a proximal end rotatably received in a proximal aperture for concurrent oscillary movement of the tubes within the chamber;

a plurality of tufts of bristles with radially exterior ends secured to the interior face of each tube and with radially interior ends defining openings for the receipt of the arms of a surgeon;

a plurality of apertures through the tubes between the tufts for the passage of cleansing/disinfectant fluid from the chamber into the tubes for cleaning the arms of a surgeon;

a drive assembly including a motor operable in an oscillatory manner secured to the distal wall with drive pulleys extending distally therefrom and with a driven pulley extending distally from each tube and with a drive belt coupling the drive pulleys and the driven pulleys;

an elastomeric washer-like member in a generally frusto-concial configuration fixedly secured to the proximal wall coaxial with the tubes for the passage of a surgeon arms there through;

a vertically disposed finger washing plate axially slidable within each tube adjacent to the distal wall, each plate having four radially extending fingers with enlarged exterior ends and with keyways formed with respect to each cylinder for receiving the exterior ends of the fingers and with coil springs within the keyways urging the exterior ends and plate proximally, the plate having proximally extending bristles for washing the fingers and fingernails of a surgeon;

four downwardly extending legs depending from the four corners of the lower wall, each leg having an upper segment and a tubular lower segment with spaced holes and slidably received over an associated upper segment and with a spring biased button extending from the upper leg through a preselected hole in the lower leg and with a stabilizing plate coupling the lower legs adjacent to their lower ends; and a horizontal adjustment rod secured to the distal wall with distally extending projections and a pair of hollow guide rails with vertical slots receiving the projections for varying the height of the housing.

2. An arm scrubbing system comprising:

a housing with an upper wall and a lower wall and a distal wall and a proximal wall and with side walls there between to define a chamber there within, two laterally spaced circular rear apertures formed in the distal wall and two laterally spaced circular proximal apertures formed in the proximal wall;

a pair of similarly configured plastic transparent tubes, each tube having a distal end rotatably received in a distal aperture and a proximal end rotatably received in a proximal aperture;

a plurality of tufts secured to the interior face of each tube defining openings;

a plurality of apertures through the tubes between the tufts for the passage of cleansing/disinfectant fluid from the chamber into the tubes for cleaning the arms of a user; and a drive assembly including a motor with drive pulleys and with driven pulleys extending distally from each tube and with a drive belt coupling the drive pulleys and the driven pulleys.

3. The system as set forth in claim 2 and further including a vertically disposed finger washing plate axially slidable within each tube adjacent to the distal wall, each plate having radially extending fingers with enlarged exterior ends and with keyways formed with respect to each cylinder for receiving the exterior ends of the fingers and with springs within the keyways urging the exterior ends and plate proximally, the plate having proximally extending bristles for washing the fingers and fingernails of a user.

4. The system as set forth in claim 2 and further including four downwardly extending legs depending from the four corners of the lower wall, each leg having an upper segment and a tubular lower segment with spaced holes and slidably received over an associated upper segment and with a spring biased button extending from the upper leg through a preselected hole in the lower leg and with a stabilizing plate coupling the lower legs adjacent to their lower ends for varying the height of the housing.

5. The system as set forth in claim 2 and further including a horizontal adjustment rod secured to the distal wall with distally extending projections and a pair of hollow guide rails with vertical slots receiving the projections for varying the height of the housing.

* * * * *